United States Patent [19]

Henderson, Jr. et al.

[11] B 3,991,092

[45] Nov. 9, 1976

[54] METAL HALIDE COMPLEXES OF 4-CYANO-2,2-DIMETHYLBUTYRALDOXIME-N-METHYLCARBAMATE

[75] Inventors: William Arthur Henderson, Jr., Stamford, Conn.; Fausto Ramirez, Goshen, Va.

[73] Assignee: American Cyanamid Company, Stamford, Conn.

[22] Filed: Mar. 27, 1974

[21] Appl. No.: 455,481

[44] Published under the second Trial Voluntary Protest Program on February 24, 1976 as document No. B 455,481.

[52] U.S. Cl. .......................... 260/429.9; 260/438.1; 260/439 R; 424/289; 424/294; 424/295
[51] Int. Cl.² ........................................... C07F 3/06
[58] Field of Search .......... 260/429.9, 438.1, 439 R, 260/465.4; 424/289, 294, 295

[56] References Cited

UNITED STATES PATENTS

| | | | |
|---|---|---|---|
| 3,621,049 | 11/1971 | Addor | 260/465.4 |
| 3,644,453 | 2/1972 | Onsager | 260/438.1 |
| 3,686,244 | 8/1972 | Marks | 260/438.1 X |

OTHER PUBLICATIONS

Lindquist, Inorganic Adduct Molecules, Academic Press, Inc., N.Y., pp. 19, 30 and 31, (1963).

*Primary Examiner*—Helen M. S. Sneed
*Attorney, Agent, or Firm*—Frank M. Van Riet

[57] ABSTRACT

Metal halide complexes of 4-cyano-2,2-dimethylbutyraldoxime-N-methylcarbamate, a method for the stabilization of said carbamate and a method for the treatment of insects and acarina with said complexes, are disclosed.

12 Claims, No Drawings

METAL HALIDE COMPLEXES OF 4-CYANO-2,2-DIMETHYLBUTYRALDOXIME-N-METHYLCARBAMATE

BACKGROUND OF THE INVENTION

The use of 4-cyano-2,2-dimethylbutyraldoxime-N-methylcarbamate (hereafter sometimes called "DIBAM") as a pesticide is disclosed in U.S. Pat. No. 3,681,505 while U.S. Pat. No. 3,621,049 discloses and claims the carbamate per se. While this compound possesses excellent insect and acarina controlling properties, it has one basic drawback. The compound has the unfortunate propensity to degrade upon storage in the solid state or in solution. This degradation is self-initiated and obviously detracts from the otherwise attractive properties of the compound as a pesticide. Although the above-cited U.S. patents (hereby incorporated herein by reference) indicate that the general class of compounds under which the 4-cyano-2,2-dimethylbutyraldoxime-N-methylcarbamate falls is storage stable, DIBAM does not possess sufficient storage stability to rate as an attractive commercial pesticide.

SUMMARY OF THE INVENTION

We have now found that DIBAM can be effectively stabilized against autodegradation by complexing the compound with copper, cobalt or zinc halides. As a complexed solid material, DIBAM does not lose its ability to effectively control insects and acarina even after storage for extended periods of time and at elevated temperatures.

DESCRIPTION OF THE INVENTION INCLUDING PREFERRED EMBODIMENTS

As mentioned above, we have discovered a novel class of complexes which have excellent storage stability and possess the ability to control insects and acarina upon dilution thereof with a suitable solvent and application of the resulting solution to plants, soil, etc. The novel complexes may also be formulated as typical wettable powder formulations that may be diluted as finished spray solutions for application to plants, soil, etc.

The novel complexes of the instant invention are produced by complexing 4-cyano-2,2-dimethylbutyraldoxime-N-methylcarbamate (DIBAM) with the copper, cobalt or zinc complexing agents.

DIBAM per se has the general structure

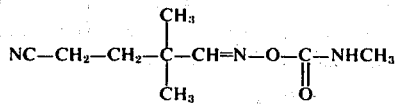

and is prepared by reacting 2,2-dimethyl-4-cyanobutyraldoxime in benzene with methyl isocyanate followed by triethylamine as disclosed in Example 10 of said U.S. Pat. No. 3,621,049.

The novel complexes of the instant invention are prepared by forming separate organic solvent solutions of the DIBAM and the complexing agent or a single solution of each, and blending the two together, preferably under anhydrous conditions. The DIBAM and the complexing agent are then reacted, the temperature ranging from about 0°C. to about 80°C. for from about 1 minute to about 24 hours and at a mole ratio of DIBAM to complexing agent of preferably about 1:1.

The solid complex is then recovered by merely removing the solvent such as by filtration, decantation, distillation, etc.

The complexing agents found useful in producing the novel complexes of the instant invention are cobalt, copper and zinc chlorides, bromides and iodides, all of which are well known in the art.

The solvents employed in the preparation of our novel complexes are, of course, governed in their usage by their ability to dissolve the metal halide involved. Useful solvents are well known, i.e. they may be found in Lange's Handbook of Chemistry, and include ethers such as diethylether; glyme; diglyme; ketones such as acetone; acetonitrile, aromatic hydrocarbons such as xylene and the like.

The solid complexes of the instant invention are generally of a powdery consistency but can range from glassy solids to waxy solids and, to this extent, the term "solid", as used herein, is meant to include the glassy, waxy or crystalline states of the complexes.

The exact mechanism by which our novel complexes are formed is not completely understood. However, while not wishing to be bound by any particular theory, it is believed that the complexing agent is, in most cases, coupled to the DIBAM through both the C≡N group and the C=O group thereof thusly:

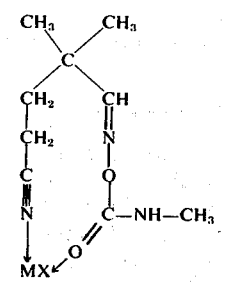

M being copper, cobalt or zinc, and X being a halogen.

As mentioned briefly above, the complexes of the instant invention are extremely stable and may be stored, as such, even at elevated temperatures over extended periods of time. They may be dissolved in an appropriate solvent, water has been found particularly useful, and these solutions may then be utilized for the control of insects and acarina as discussed in the above cited U.S. Pat. No. 3,681,505. More particularly, the DIBAM complexes are particularly effective against aphids, mites and ticks.

The complexes may also be applied to the foliage of plants as dusts, in addition to their use as liquid sprays, to protect them from insects and mites which feed thereon and they may also be incorporated in or applied to soil in order to protect germinating and growing plants from soilborne pests which attack the root systems and stems of said plants. The DIBAM complexes may also be applied to the breeding sites of pests to control both the larvae and adult stages of breeding pest populations. The complexes, as above, may be applied in conventional formulations such as dusts, dust concentrates, granular materials, wettable powders, and the like. They may be employed as emulsions to which suitable surfactants, wetting agents or emulsifiers have been added or may be applied on inert solid carriers such as talcs and clays e.g. kaolin clay, fuller's earth, atapulgite clay, etc., or or chalk, diatomaceous earth, wood flour, silica, charcoal, activated carbon or other inert powders.

It is generally preferred that the novel complexes of the instant invention be used as a wettable powder. As such, generally from about 25% to about 95% of the complex, from about 2% to about 10% of any known dispersing agent, from about 2% to about 10% of any known wetting agent, the remainder being an inert solid, carrier such as those mentioned above, all percentages being by weight based on the total weight of the formulation may be used. Either the wetting agent or the dispersing agent may be omitted from the formulation, but not both. In such an event, double the specified amount of the included material may be used.

The following examples are set forth for purposes of illustration only and are not to be construed as limitations on the present invention except as set forth in the appended claims.

EXAMPLE 1

To 0.1 mole of 4-cyano-2,2-dimethylbutyraldoxime-N-methylcarbamate (DIBAM) dissolved in 30 ml of chloroform and 100 ml of dry ether in a suitable reaction vessel under nitrogen is added with stirring 0.1 mole of anhydrous zinc chloride dissolved in 100 ml of dry ether. A colorless oil is thrown down which, on stirring for 1 hour, crystallizes to give a fine, white powder. The resultant mixture is filtered under nitrogen, washed twice with 100 ml portions of dry ether, and dried under vacuum. A 1:1 complex of DIBAM-$ZnCl_2$ is obtained in 97–99% yield. The melting point of the complex is 122°–124°C.

A portion of the complex is decomposed by addition thereof to water. Active DIBAM is recovered unchanged and in quantitative yield. The remainder of the complex is stored in a sealed container at 50°C. for 15 days, after which the active DIBAM is recovered by addition of the complex to water in 94–95% yield. DIBAM per se stored under the same conditions is recovered in only 15% yield.

EXAMPLE 2

Using a reaction vessel as in Example 1, an equimolar amount of zinc chloride dissolved in dry acetone is added to DIBAM dissolved in dry acetone. Complex is formed when most of the acetone is removed, either by distillation or by evaporation under reduced pressure, as in Example 1. The complex is isolated as in Example 1, and has the same properties.

EXAMPLE 3

The procedure of Example 2 is again followed except that the acetone used to dissolve the DIBAM is replaced by xylene. Identical results are achieved.

EXAMPLES 4–7

Using the methods described in Examples 1 and 2, various DIBAM complexes are prepared in essentially quantitative yield, and their physical properties and stabilities determined. The results are set forth in Table I, below.

TABLE I

| Example | Complexing Agent | Method of Example Number | Physical Properties | % Active DIBAM Recovery After — Days at 50°C. | | |
|---|---|---|---|---|---|---|
| | | | | 0 | 15 | 30 |
| 4 | $ZnBr_2$ | 1 | White powder (mp 144–146°) | 87 | 85 | 78 |
| 5 | $ZnI_2$ | 2 | White powder (mp 138–141°) | 100 | 82 | 70 |
| 6 | $CoCl_2$ | 1 | Blue glass | 100 | 72 | — |
| 7 | $CuCl_2$ | 1* | Green powder (mp 118–120°) | 84 | 91 | — |

*Acetonitrile used as solvent.

EXAMPLES 8–11

Following the procedure of Example 1 other metal halides are complexed with DIBAM. In each instance, quantitative yields of the complex are recovered in solid form. The complexes are extremely stable. The results are set forth in Table II, below.

TABLE II

| Example | Complexing Agent |
|---|---|
| 8 | $CoI_2$ |
| 9 | $CuBr_2$ |
| 10 | $CuI_2$ |
| 11 | $CoBr_2$ |

EXAMPLE 12

The zinc complex of Example 2 is stored at 37°C. in a sealed container for 60 days. The percent recovery of DIBAM is 99%. When DIBAM is similarly stored for 30 days, the percent recovery is only 74%.

EXAMPLE 13

The zinc complex of Example 3 is admixed (50%, by weight) with 4.0%, by weight, of a commerically available dispersing agent, 1.0%, by weight, of a commercially available wetting agent and 45.0%, by weight, of kaolin clay. Storage of the resultant wettable powder formulation at 50°C. for the following number of days, results in the recovery of the specified amount of active DIBAM: 0 days — 100%; 15 days — 100%; 30 days — 94%. The efficacies of the DIBAM per se and the wettable powder of this example, all things being equal, in their use as pesticides, are identical.

EXAMPLE 14

The procedure of Example 13 is again followed except that 80.0% of the zinc complex and 15.0% of diatomaceous earth, as a replacement for the kaolin, are used. Stability tests show: 0 day — 100%; 15 days — 97%; 30 days — 73%. As pesticides, DIBAM per se and the wettable powder of this example, under identical conditions, function equivalently.

EXAMPLE 15

Again following the procedure of Example 13 except that the kaolin is replaced by 45% of atapulgite clay, the following results are attained: 0 days — 100%; 15 days — 91%; 30 days — 79%. Miticide efficiencies for the wettable powder of this example and DIBAM per se, all variables held equal, are identical.

EXAMPLE 16 (COMPARATIVE)

Efficacy Against Mites and Aphids

The efficacy of 4-cyano-2,2-dimethylbutyraldoxime-N-methylcarbamate against mites and aphids is demonstrated in accordance with the following test procedures.

1. Bean Aphid — Aphis fabae Scopoli

Compounds are tested as solutions in 65 percent acetone-35 percent water. Two-inch pots, each containing a nasturtium plant 2 inches high and infested with about 150 aphids 2 days earlier, are placed on a turntable (4 rpm) and sprayed for two revolutions with a No. 154 De Vilbiss Atomizer at 20 psi air pressure. The spray tip is held about 6 inches from the plants and the spray is directed so as to give complete coverage of the aphids and the plants. The sprayed plants are laid on their sides on white enamel trays. Mortality counts are made after holding for one day at 70°F. and 50% r.h.

LC-50 values are obtained in the standard manner by plotting percent mortality as a function of the compound concentration for a variety of concentrations. The term LC-50 means the compound concentration expressed in ppm required to kill 50 percent of the aphids.

2. Two-Spotted Spider Mite - *Tetranychus urticae* (Koch)

Sieva lima bean plants with primary leaves 3 to 4 inches long are infested with about 100 adult mites per leaf 4 hours before use in this test. The mite and egg infested plants are dipped for three seconds in the solutions used in the above test, and the plants set in the hood to dry. They are held for two days at 80°F., 60% r.h., and the adult mite mortality counted on one leaf under a stereoscopic microscope. The other leaf is left on the plant an additional five days and then examined at 10X power to estimate the kill of eggs and of newly-hatched nymphs, giving a measure of ovicidal and residual action, respectively.

Since mites are known to develop resistance to phosphorus containing insecticides, the carbamate is also tested against a strain of "phosphate resistant" mites, as described below.

3. "Phosphate-Resistant" Mites

The phosphate-resistant colony of two-spotted spider mites (Tetranychus urticae [Koch]) used are subjected to repeated treatments with a 1:1:1 mixture of dimethoate, malthion and parathion periodically over a period of 9 years. $LD_{50}$ tests showed this colony to be approximately 50 times more resistant to these chemicals than the susceptible colony. The carbamate is tested against these phosphate-resistant mites following the same procedure used for the susceptible mites.

Mite LC-50 values are determined in the manner described above or aphid LC-50 values.

4. Mite Systemic Tests

The carbamate is formulated as an emulsion containing 0.1 gram of carbamate, 0.2 gram of Alrodyne 315 emulsifier, 10 ml of acetone and 90 ml of water. This is diluted ten-fold with water to give a 100 ppm emulsion for the test. A sieva lima bean plant with only the primary leaves unfolded is cut off just above soil level and inserted into a 2 ounce bottle of 100 ppm emulsion and held in place by a bit of cotton wrapped around the stem. The bottle is then placed in a ventilated box with the leaves extending outside the box, such that any possible fumes from the carbamate will be drawn out the end of the box rather than rising to affect the test leaves. About 50 adult two-spotted spider mites are placed on each leaf. After holding three days at 80°F. and 60% r.h., mortality estimates are made.

The percent kill of the carbamate of the aphids, spider mites, phosphate-resistant mites at 1000 ppm, 100 ppm and 10 ppm is 100% in each instance. The LC-50 values (ppm) are 0.8, 3–5 and 2–4, respectively. Systemic kill at 100 ppm is 100%.

EXAMPLES 17–25

When the testing procedures of Example 16C are performed utilizing the complexes of the instant invention, as represented by Examples 2, 4, 5, 6, 7, 8, 9, 10 and 11, in each instance as a replacement for the 4-cyano-2,2-dimethylbutyraldoxime-N-methylcarbamate of Example 16C, the percent kill of aphids, susceptible mites and phosphate-resistant mites is identical to that of the carbamate for each of the nine complexes tested, i.e. 100%.

EXAMPLE 26 (COMPARATIVE)

Efficacy Against Insects

The efficacy of the 4-cyano-2,2-dimethylbutyraldoxime-N-methylcarbamate against insects is demonstrated in accordance with following test procedures.

1. Large Milkweed Bug - *Oncopeltus fasciatus* Dallas

The carbamate is formulated as a 1 percent dust by mixing 0.1 gram of the carbamate with 9.9 grams of Pyrax ABB talc, wetting with 5 ml of acetone and grinding with a mortar and pestle until dry. 25 Mg of the 1 percent dust is sprinkled evenly over the glass bottom of a 7-inch diameter cage, using a screen-bottom plastic cup about five-eights inch in diameter as an applicator, giving a deposit of approximately 0.108 mg./sq. cm. of the 1 percent dust. Water is supplied in a 2-ounce bottle with a cottom wick, twenty adult bugs are added and a screen cover is placed on the top. Mortality counts are made after holding for three days at 80°F. and 60% r.h.

2. Housefly – *Musca domestica* Linnaeus

Groups of 25 adult female houseflies are lightly anesthetized with $CO_2$, placed in wide-mouthed pint mason jars, and covered with a screen cap. The carbamate is formulated as an emulsion containing 0.1 gram of carbamate, 0.2 gram of Alrodyne 315 emulsifier, 10 ml of acetone and 90 ml of water. Two milliliters of this emulsion are diluted to 40 ml with 10 percent sugar solution in a 10-gram glass vial, giving a concentration of 50 ppm. The mouth of the vial is covered with a single layer of cheesecloth, inverted and placed on the screen cap, so that the flies can feed on the solution through the screen. Mortality counts are made after 2 days at 80°F.

The carbamate kills 100 percent of the milkweed bugs and 100 percent of the houseflies.

EXAMPLES 27–35

Following the procedure of Example 26C, the complexes of the instant invention, specifically those of Examples 2 and 4–11 are tested against milkweed bugs and houseflies as set forth therein. In each instance, the complexes kill 100% of the milkweed bugs and 100% of the houseflies.

Formulations of the novel complexes of the instant invention containing 25–95% of the active ingredient, i.e. complex and 5–75% of a horticultural adjuvant, e.g. known solid or liquid carriers, formulation aids or the like may be used to control pests according to the instant invention.

The formulations may be applied to the locus or habitat (i.e. foliage and soil etc.) where the pests may congregate, as well as to pests themselves e.g. insects and acarina.

We claim:

1. The solid metal halide complex of 4-cyano-2,2-dimethylbutyraldoxime-N-methylcarbamate wherein said metal is cobalt, copper or zinc.

2. The complex of claim 1 wherein said metal is zinc.

3. The complex of claim 1 wherein said metal halide is zinc chloride.

4. The complex of claim 1 wherein said metal halide is zinc bromide.

5. The complex of claim 1 wherein said metal halide is cupric chloride.

6. The complex of claim 1 wherein said metal halide is cobalt chloride.

7. A method for the stabilization of 4-cyano-2,2-dimethylbutyraldoxime-N-methylcarbamate which comprises (1) contacting (A) an organic solvent solution of 4-cyano-2,2-dimethylbutyraldoxime-N-methylcarbamate with (B) an organic solvent solution of a metal halide selected from the group consisting of copper, cobalt and zinc halide at a temperature ranging from about 0°C. to about 80°C. for from about 1 minute to about 24 hours and at a ratio of (A) : (B) of about 1 : 1 and (2) recovering the resultant product.

8. A method according to claim 7 wherein said metal halide is zinc.

9. A method according to claim 7 wherein said metal halide is zinc chloride.

10. A method according to claim 7 wherein said metal halide is zinc bromide.

11. A method according to claim 7 wherein said metal halide is cupric chloride.

12. A method according to claim 7 wherein said metal halide is cobalt chloride.

* * * * *